(12) United States Patent
Al Mortadi

(10) Patent No.: US 10,888,451 B2
(45) Date of Patent: Jan. 12, 2021

(54) ORAL DEVICE FOR PREVENTING SLEEP APNEA AND A METHOD OF MANUFACTURING

(71) Applicant: Noor Abdullah Al Mortadi, Amman (JO)

(72) Inventor: Noor Abdullah Al Mortadi, Amman (JO)

(73) Assignee: Jordan University of Science and Technology, Irbid (JO)

(*) Notice: Subject to any disclaimer, the term of this patent is extended or adjusted under 35 U.S.C. 154(b) by 198 days.

(21) Appl. No.: 15/849,073

(22) Filed: Dec. 20, 2017

(65) Prior Publication Data

US 2018/0168851 A1 Jun. 21, 2018

Related U.S. Application Data

(60) Provisional application No. 62/436,701, filed on Dec. 20, 2016.

(51) Int. Cl.
| | | |
|---|---|---|
| *A61F 5/56* | (2006.01) | |
| *A61C 9/00* | (2006.01) | |
| *A61C 7/36* | (2006.01) | |
| *A61C 7/00* | (2006.01) | |

(52) U.S. Cl.
CPC ............. *A61F 5/566* (2013.01); *A61C 7/002* (2013.01); *A61C 7/36* (2013.01); *A61C 9/0053* (2013.01); *A61C 9/004* (2013.01)

(58) Field of Classification Search
CPC ...... A61F 5/56; A61F 5/566; A61F 2005/563; A61F 2/3099; A61F 2002/30991; A61C 7/08; A61C 7/36; A61C 7/002; A61C 9/004; A61C 9/0053
See application file for complete search history.

(56) References Cited

U.S. PATENT DOCUMENTS

| | | | | |
|---|---|---|---|---|
| 6,505,625 | B1 * | 1/2003 | Uenishi | A61C 7/08 |
| | | | | 128/848 |
| 6,895,970 | B1 * | 5/2005 | Lawrence | A61F 5/566 |
| | | | | 128/848 |
| 8,113,206 | B2 * | 2/2012 | Roettger | A63B 71/085 |
| | | | | 128/846 |
| 2012/0073582 | A1 * | 3/2012 | Kopp | A61F 5/566 |
| | | | | 128/848 |
| 2015/0202075 | A1 * | 7/2015 | Vincent | A61C 7/36 |
| | | | | 128/848 |

* cited by examiner

*Primary Examiner* — Rachael E Bredefeld
*Assistant Examiner* — Camtu T Nguyen
(74) *Attorney, Agent, or Firm* — Dunlap Bennett & Ludwig, PLLC

(57) ABSTRACT

An oral device for preventing sleep apnea is provided. The oral device maintains an opening between the anterior teeth, resulting in a wider upper airway, while allowing the mouth to also open for yawning and normal talking. The oral device provides an upper plate and lower plate, each adapted to retain the biting surface of the respective set of maxilla and mandible teeth, wherein curved rods pivotally interconnecting both plates are adapted for maintaining an operable spaced apart relationship therebetween. The oral device is a unitary construction made from FDA-approved elastomers.

6 Claims, 2 Drawing Sheets

ORAL DEVICE FOR PREVENTING SLEEP APNEA AND A METHOD OF MANUFACTURING

CROSS-REFERENCE TO RELATED APPLICATION

This application claims the benefit of priority of U.S. provisional application No. 62/436,701, filed 20 Dec. 2016, the contents of which are herein incorporated by reference.

BACKGROUND OF THE INVENTION

The present invention relates to medical devices and, more particularly, an oral medical device for preventing sleep apnea and a method of manufacturing the same.

Sleep apnea affects people when the tongue blocks the air flow during sleep, decreasing the oxygen transferred to the blood, affecting the snoring habits of people so afflicted. It is important for oral devices for preventing sleep apnea to be of a unitary construction, otherwise a separable component could become dislodged while the patient sleeps, effecting obvious health risks. Current unitary devices, however, have the following flaws: (a) some cannot withstand the heat needed for sanitary cleaning and sterilization, requiring more complex cleaning or sterilization processes; (b) others have metal hinges which provides areas conducive for bacteria growth, leading to infections; (c) yet other unitary devices, for example the CPAP, is noisy, big and heavy for carrying on travels, as well as being very difficult to clean and maintain; (d) some unitary plastic devices have excessive surface area and/or overlapping pieces providing excessive breeding grounds and/or holding places for saliva for bacterium growth; and (e) some are not designed for the optimal predetermined medical position of the user's lower jaw.

As can be seen, there is a need for a unitary oral device for preventing sleep apnea, wherein the oral device affects a mandible posture to hold the tongue forward, creating an opening between the anterior teeth to widen the upper airway, while still allowing the mouth to open for yawning and normal talking, and wherein the oral device is tailored to the oral cavity of each user through an intraoral scan. The unitary oral device may be manufactured via additive manufacture of an FDA approved elastomer which tolerates heat and chemicals for disinfecting purposes.

SUMMARY OF THE INVENTION

In one aspect of the present invention, an oral device for preventing sleep apnea including an upper plate adapted to conform to or engage a biting surface of maxilla teeth of a user; a lower plate adapted to conform to or engage a biting surface of mandible teeth of the user; and two rods, each rod operative associated with both an anterior portion and a posterior portion of the lower plate and upper plate, respectively.

In another aspect of the present invention, the oral device for preventing sleep apnea includes an upper plate adapted to conform to a biting surface of maxilla teeth of a user; a lower plate adapted to conform to a biting surface of mandible teeth of the user; an indexed bite plate along each of the two anterior, upward-facing surfaces of the lower plate, herein each indexed bite plate is shaped to accept cusp tips of the maxilla teeth; and two S-shaped rods, each S-shaped rod pivotally connected with both an anterior portion of the upper plate and a posterior portion of the lower plate, wherein each S-shaped rod curves outward when extending from the anterior portion to the posterior portion, wherein each anterior portion is adapted to be adjacent to incisor or canine teeth of the user, and wherein each posterior portion is adapted to be adjacent to a first molar teeth of the user.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides an oral device for preventing sleep apnea by maintaining an opening between the anterior teeth, resulting in a wider upper airway, while allowing the mouth to also open for yawning and normal talking. The oral device provides an upper plate and lower plate, each adapted to retain the biting surface of the respective set of maxilla and mandible teeth, wherein curved rods pivotally interconnecting both plates are adapted for maintaining an operable spaced apart relationship therebetween. The oral device is a unitary construction made from FDA-approved elastomers.

Figure 1:
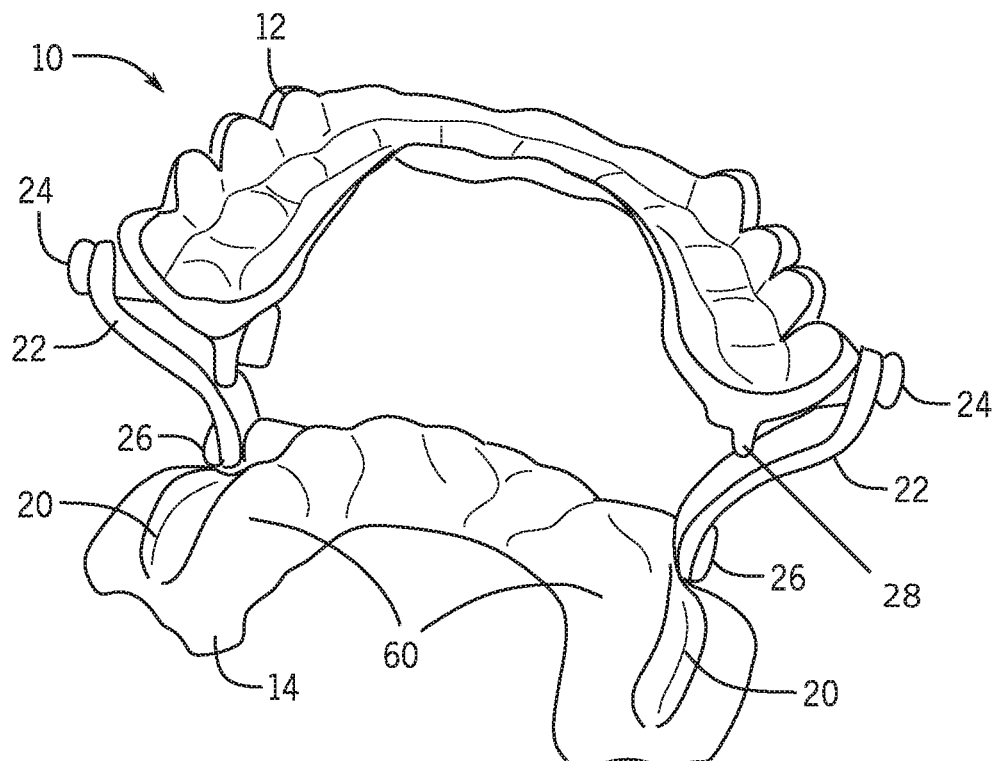
FIG. 1 is a rear perspective view of an exemplary embodiment of the present invention.
Figure 2:
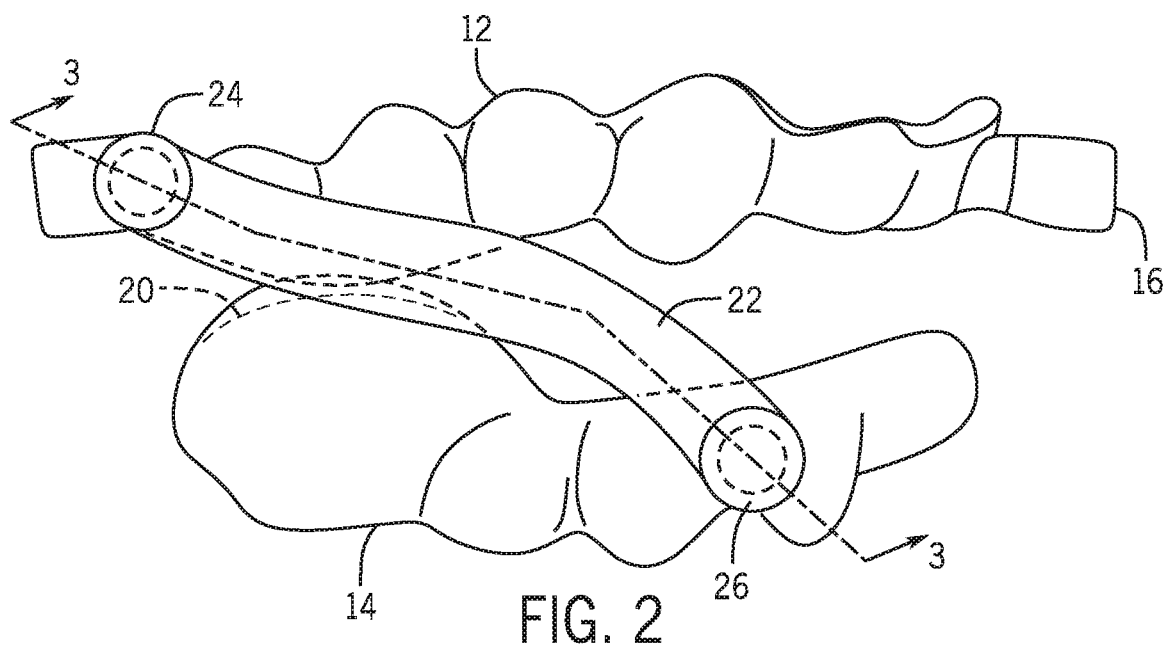
FIG. 2 is a side view of an exemplary embodiment of the present invention.
Figures 3, 4:
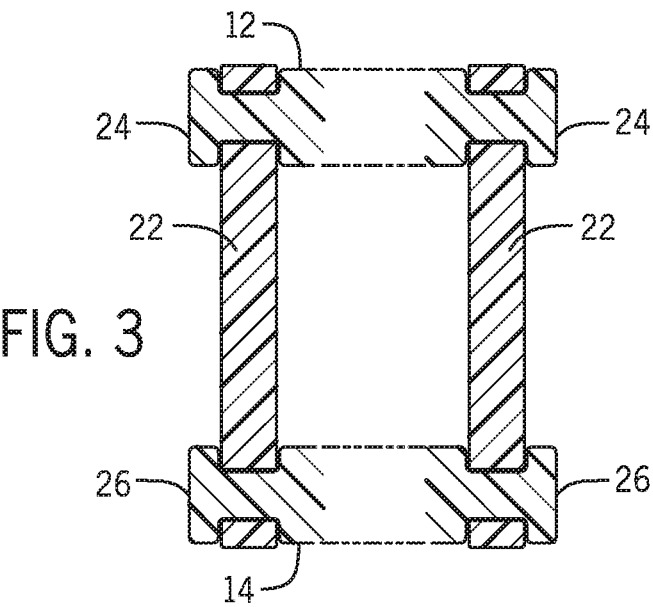
FIG. 3 is a cross-sectional view of an exemplary embodiment of the present invention, taken along line 3-3 of FIG. 2.
FIG. 4 is a flowchart of an exemplary embodiment of the present invention.

Referring now to FIGS. 1 through 3, the present invention may include an oral device 10 for preventing sleep apnea, wherein the oral device 10 may be a unitary construction formed from FDA-approved elastomers. The FDA-approved elastomers could provide an operable surface impregnated with an antimicrobial agent to assure cleanliness. The oral device 10 may include an upper plate 12 and a lower plate 14 spaced apart by curved rods 22. The upper plate 12 may be dimensioned and adapted to snugly conform to the biting surface of the teeth of the maxilla or upper jaw of a user. The lower plate 14 may be dimensioned and adapted to snugly conform to the biting surface of the teeth of the mandible or lower jaw of a user. As a result, both the upper and the lower plates 12 and 14 have an arcuate shape. The lower or upper plates 12 or 14 may provide a protruding finger tab 16 for manipulating the oral device 10 during use with one's fingers.

In certain embodiments, the two curved rods 22 provide a posterior operative association to the lower plate 14 at or adjacent to a portion thereof adapted to receive the opposing cuspid teeth of a user. These two curved rods 22 extend to provide an anterior operative association to the upper plate 12 at or adjacent to a portion thereof adapted to receive the opposing incisor or canine teeth of the user. The two curved rods 22 may be dimensioned and adapted to maintain a predetermined spatial relationship between the upper and lower plates 14 and 12. Such a spatial relationship may be defined by a dental professional regarding (a) how far the lower jaw should be set advanced relative to the upper jaw, and/or (b) for keeping the user's lower jaw and hence tongue extended during use, keeping the airway open and eliminating snoring. Each connection point of the curved rods 22 may be pivotal connections 24 and 26, the posterior pivot 24 and the anterior pivot 26, respectively.

Posterior bite plates 60 may be provided and molded onto the lower plate 14 in order to maintain a spaced apart relationship between the upper and lower plates 12 and 14. The upward-facing surface portion of the posterior bite plates 60 may be indexed 20 to accept the cusp tips 28 of a downward-facing surface of the upper plate, thus maintaining the jaw in the same position and preventing lateral excursion (sideward movement of the mandible). The posterior bite plates 60 may range in height, in certain embodiments, 2 mm in height, depending on the user's respiratory needs and/or how far the user's jaw needs to be opened. The placement of the posterior bite plates 60 at or near the first molar may provide a wider airway than if the posterior hinges were mounted on the lower jaw (mandible).

The alignment of the upper and lower plates 12 and 14 may also be maintained by the curved rods 22 so that the lower jaw of the user is in the corrected occlusion (edge to edge). The curved rods 22 are made of a material of sufficient strength to hold the lower jaw forward consistently. The curved rods 22 may form a S-shape, rather than linear and flat, so they are in contour with the cheek, providing more comfort than having hinges and bars that interfere with the shape of the cheek. The pivotal connections 24 and 26 may be integrated solid rotational hinges which are adapted to minimize the lateral excursion thereby avoiding irritating temporomandibular joint (TMJ) disorders, while still allowing the mouth to open for yawning and normal talking.

As an additional benefit, the present invention tends to prevent users from grinding their teeth.

The present invention may include at least one computer with a user interface. The computer may include at least one processing unit and a form of memory including, but not limited to, a desktop, laptop, and smart device, such as, a tablet and smart phone. The computer includes a program product including a machine-readable program code for causing, when executed, the computer to perform steps. The program product may include software which may either be loaded onto the computer or accessed by the computer. The loaded software may include an application on a smart device. The software may be accessed by the computer using a web browser. The computer may access the software via the web browser using the internet, extranet, intranet, host server, internet cloud and the like.

Referring to FIG. 4, a method of manufacturing the present invention may include the following. An individual, such as a dentist, dental technician, or the like may perform an intraoral scan or classic impression and modeling of the patient's oral cavity so as to provide anatomical data points defining the physical size and shape. The preferred method is to scan the mouth (the teeth and surrounding tissues) using an intraoral scanner. The 3D image of the mouth and the anatomical data points thereof will appear on the intraoral scan or the representation thereof on a computer's screen or user interface. When the person taking the image is satisfied with the clarity and completeness of the picture, he or she transmits the image to the designer. When an intraoral scanner is not available, an impression is taken of the full mouth with dental impression material and then a casting is made in an appropriate material, such as gypsum. This model can either be transmitted to the dentist's or to the lab. This information is then transmitted to the designer. Also, the anatomical data points obtained from the scans can be used for other dental appliances or restoration devices.

The designer imports the scan information incorporating the anatomical data points into the design program and creates the custom design for the client. Then the design is exported to the 3D printer for manufacturing and finishing. Through a software application and/or program product, a digital or computer-aided design of upper and lower plates and hinges is enabled. The software program is any program which is a computer aided design program, which takes data about the client's mouth and produces an instruction file for use by a manufacturing unit. Then the individual may use additive manufacture or 3D printing for forming the oral device using FDA-approved elastomers tailored to the abovementioned anatomical data points. The plates 12, 14 and rods 22 may be molded as an assembly, wherein the protrusion forces used to provide a unitary construction has to be consistent to avoid irritating the TMJ. Finishing and other process steps to significantly reduce the amount of residue may be employed. The finished item is then sent to the technician/dentist to instruct the patient how to use this device.

A method of using the present invention may include the following. The oral device 10 disclosed above may be provided. A user may clean the oral device 10 before use. Next, the user opens their mouth to insert the oral device 10, placing the lower plate 14 onto lower teeth, then moving the flex lower jaw forward, and biting into the upper plate 12. The user may then close the mouth to make sure the plates fully fit. Once the person has properly cleaned and fit the oral device 10 into his or her mouth, they are ready to breathe normally and go to sleep. After getting up, the clients should remove the oral device 10 and rinse the body fluids off the oral device 10 before putting it into the storage container.

The oral device 10 is replaceable for users over the age of 16 years old because of all the fittings and all of the detailed dimensions used to make the computer assisted design may be retained by the dental lab on the computer.

The computer-based data processing system and method described above is for purposes of example only, and may be implemented in any type of computer system or programming or processing environment, or in a computer program, alone or in conjunction with hardware. The present invention may also be implemented in software stored on a computer-readable medium and executed as a computer program on a general purpose or special purpose computer. For clarity, only those aspects of the system germane to the invention are described, and product details well known in the art are omitted. For the same reason, the computer hardware is not described in further detail. It should thus be understood that the invention is not limited to any specific computer language, program, or computer. It is further contemplated that the present invention may be run on a stand-alone computer system, or may be run from a server computer system that can be accessed by a plurality of client computer systems interconnected over an intranet network, or that is accessible to clients over the Internet. In addition, many embodiments of the present invention have application to a wide range of industries. To the extent the present application discloses a system, the method implemented by that system, as well as software stored on a computer-readable medium and executed as a computer program to perform the method on a general purpose or special purpose computer, are within the scope of the present invention. Further, to the extent the present application discloses a method, a system of apparatuses configured to implement the method are within the scope of the present invention.

It should be understood, of course, that the foregoing relates to exemplary embodiments of the invention and that modifications may be made without departing from the spirit and scope of the present invention.

What is claimed is:

1. A device, comprising:
    an upper plate having a plurality of anatomical data points adapted to conform to a biting surface of maxilla teeth of a user;
    a lower plate having a plurality of anatomical data points adapted to conform to a biting surface of mandible teeth of the user;
    an indexed bite plate along each side of two posterior, upward-facing surfaces of the lower plate, wherein each indexed bite plate is shaped to accept cusp tips of a downward-facing surface of the upper plate; and
    two S-shaped rods, each S-shaped rod connecting posterior portion of the upper plate and an anterior portion of the lower plate, wherein each S-shaped rod has a first curve adjacent the posterior portion of the upper plate and a second curve adjacent the anterior portion of the lower plate, the two curves defining a non-linear S-shaped.

2. The device of claim 1, wherein each indexed bite plate extends approximately two millimeters upwardly from said posterior, upwardly-facing surface.

3. The device of claim 1, wherein each anterior portion is adapted to be adjacent to incisor or canine teeth of the user.

4. The device of claim 1, wherein each posterior portion is adapted to be adjacent to first molar teeth of the user.

5. The device of claim 1, wherein each S-shaped rod is pivotably connected to the respective anterior and posterior portions.

6. The device of claim 1, further comprising a finger tab protruding from one of either the upper or lower plate.

* * * * *